United States Patent
Anderson et al.

(10) Patent No.: US 6,221,087 B1
(45) Date of Patent: Apr. 24, 2001

(54) ABLATION ASSEMBLY WITH SAFETY STOP

(75) Inventors: David M. Anderson, Seattle; Robert L. Barry, Kirkland, both of WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/411,137

(22) Filed: Oct. 1, 1999

(51) Int. Cl.$^7$ .................................................. A61B 17/22
(52) U.S. Cl. ........................................... 606/159; 606/180
(58) Field of Search .................................. 606/159, 170, 606/158, 1, 178, 171, 180, 113, 127

(56) References Cited

U.S. PATENT DOCUMENTS

| | | |
|---|---|---|
| 4,445,509 | 5/1984 | Auth . |
| 4,771,774 | 9/1988 | Simpson et al. . |
| 4,781,186 | 11/1988 | Simpson et al. . |
| 4,842,579 | 6/1989 | Shiber . |
| 4,898,575 | 2/1990 | Fischell et al. . |
| 5,019,089 * | 5/1991 | Farr ....................................... 606/172 |
| 5,409,859 | 4/1995 | Glass et al. . |
| 5,415,170 | 5/1995 | Hammerslag et al. . |
| 5,486,177 * | 1/1996 | Mumme et al. ........................ 606/79 |
| 5,667,490 | 9/1997 | Keith et al. . |
| 5,779,722 | 7/1998 | Shturman et al. . |
| 5,871,487 * | 2/1999 | Warner et al. ........................ 606/130 |
| 5,893,857 | 4/1999 | Shturman et al. . |

* cited by examiner

Primary Examiner—Henry J. Recla
Assistant Examiner—Lien Ngo
(74) Attorney, Agent, or Firm—Christensen O'Connor Johnson Kindness PLLC

(57) ABSTRACT

An ablation assembly has an advancer mechanism coupled to a proximal end of a driveshaft, and an ablation device, such as a rotatable burr, coupled to a distal end of the driveshaft. The advancer mechanism is moveable from a first position forward along a path of motion, the ablation device being advanced as the advancer mechanism is moved forward. A stop extends into the path of motion of the advancer mechanism by a sufficient amount to stop the forward motion of the advancer mechanism when it contacts the stop. The stop is secured at a location spaced forward from the starting position of the advancer mechanism by a distance equal to the length of a lesion to be ablated.

4 Claims, 3 Drawing Sheets

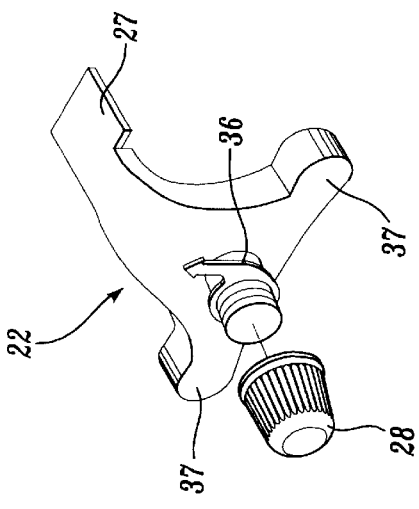
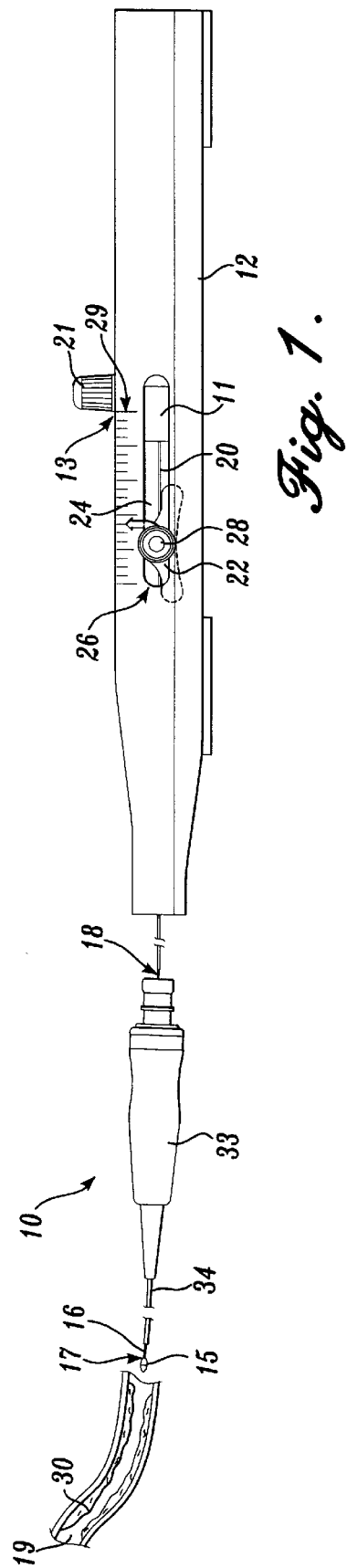

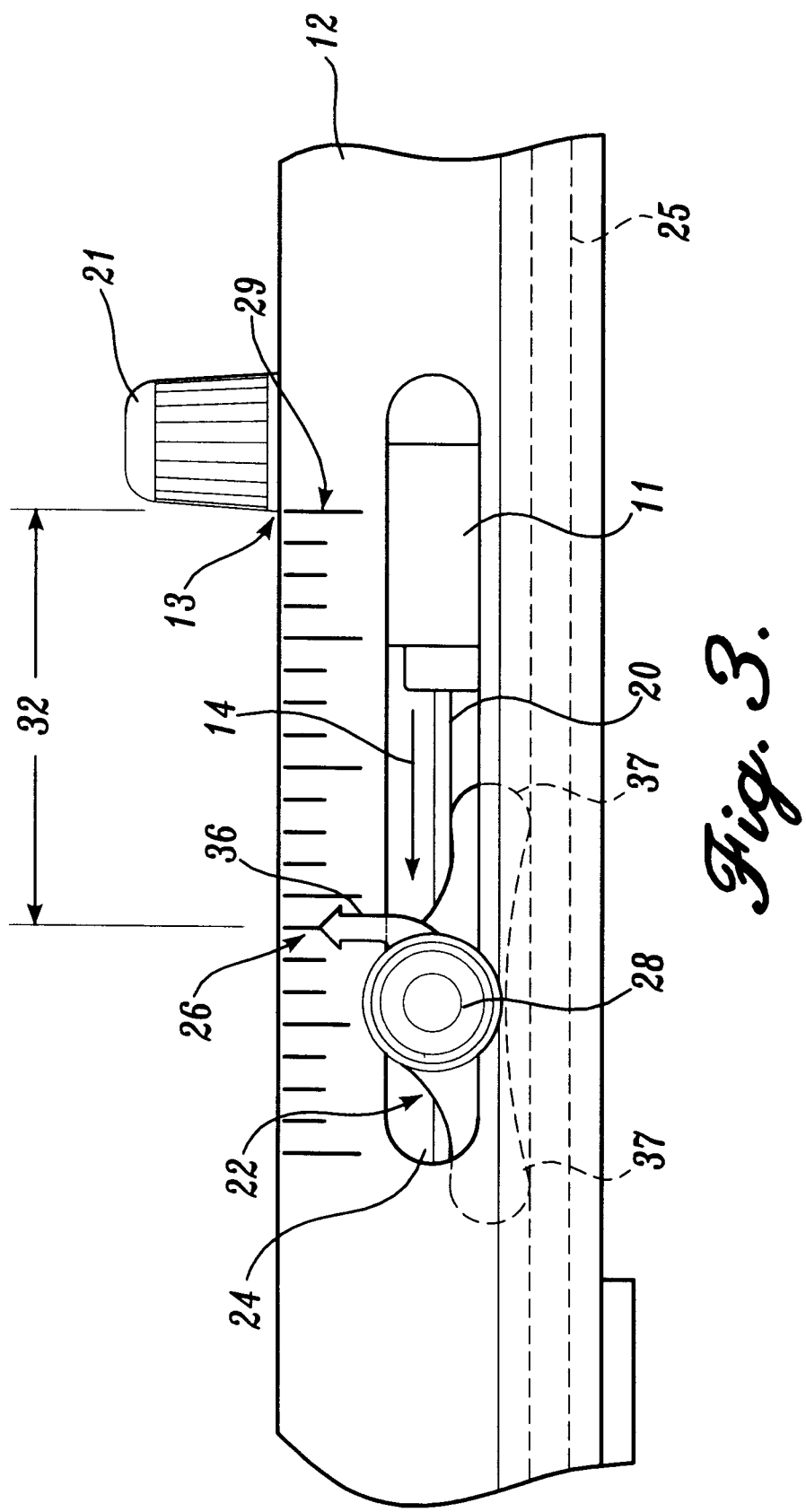

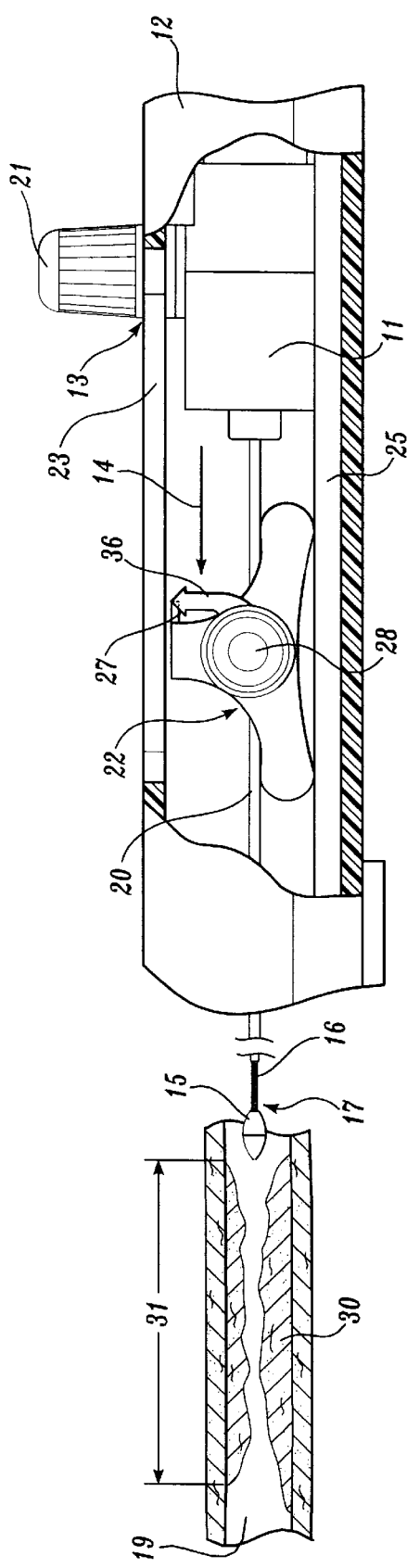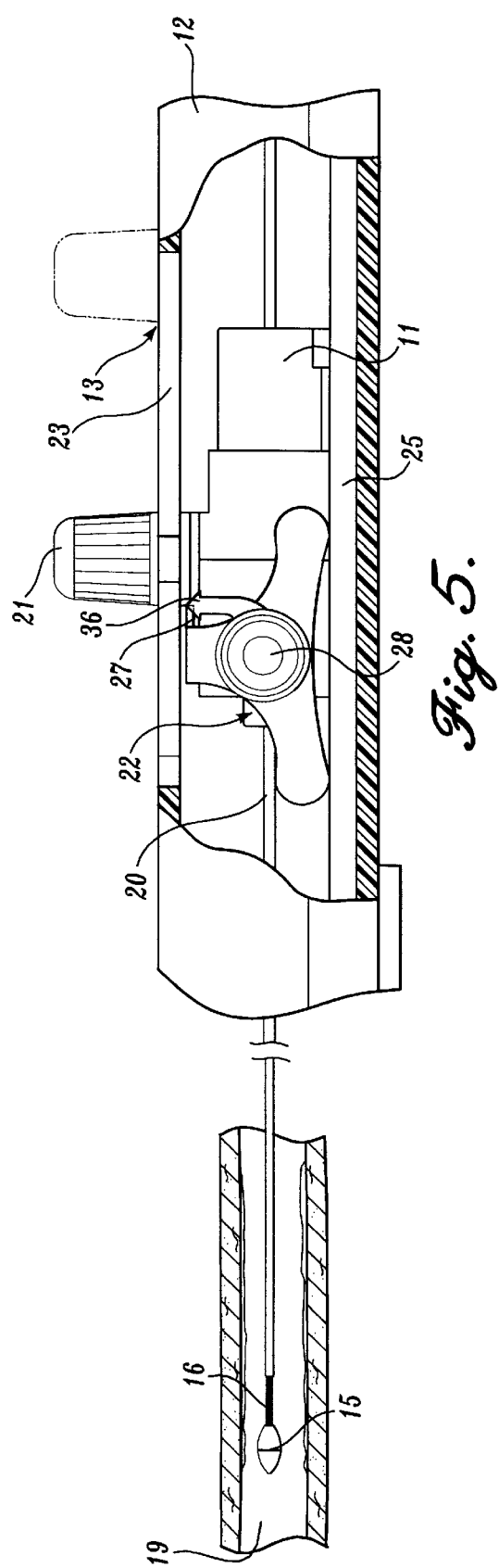

ABLATION ASSEMBLY WITH SAFETY STOP

FIELD OF THE INVENTION

This invention relates to a method and apparatus for ablating unwanted material from a patient's vasculature.

BACKGROUND OF THE INVENTION

Vascular diseases, such as atherosclerosis and the like, have become quite prevalent in the modern day. These diseases may manifest themselves in a number of ways, often requiring different forms or methods of treatment for curing the adverse effects of the diseases. For example, vascular diseases may take the form of deposits or growths in a patient's vasculature which may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies have been developed. For example, treatment devices have been developed that remove the material occluding a vascular lumen. Such treatment devices, sometimes referred to as atherectomy devices or ablation devices, use a variety of material removal means, such as rotating cutters or ablaters for example, to remove the occluding material. (The term "atherectomy device" as used in the specification refers to ablation devices for use in any portion of a patient's vasculature. Thus, while the atherectomy devices provided in accordance with preferred embodiments of the present invention are well suited for use in the coronary arteries, their use is not limited to the coronary arteries.) The material removal device, such as a rotatable burr, is typically rotated via a driveshaft that extends out of the vasculature of the patient and to an electric motor.

In operation, an ablation device is typically advanced over a guide wire placed in vivo until the material removal device is positioned just proximal to the occluded site. The motor is used to rotate the driveshaft and the material removal device, and the material removal device is moved through the occluded vessel. The material removal device removes the material from the vessel, rather than merely displacing or reforming the material as in a balloon angioplasty procedure.

Although such types of ablation devices provide desirable results, it is sometimes difficult to operate them strictly within preferred operating parameters. For example, it is desirable to only operate the material removal device while it is in contact with the lesion to be ablated. However, with conventional systems, once the ablation device works through a distal end of the lesion, the sudden lack of resistance causes the ablation device to dart forward. Such darting may result in unwanted ablation of a vessel wall, and is typically accompanied by an undesirably large rpm drop. More particularly, when in use, a material removal device, such as a rotatable burr, is spun at approximately 180,000 rpm. When the burr engages the lesion or unwanted deposits, the ablation process causes a drop of approximately 5,000 rpm. It is desirable to maintain a consistent rpm drop of approximately 5,000 during ablation of the lesion. If an excessive rpm drop occurs, it is typically accompanied by increased torque and an undesirable increase in heat, as well as an increase in quantity and size of particles generated by the ablation. Furthermore, if the ablation device darts forward far enough, it may engage a spring tip located at a distal end of a guide wire. The friction caused by the rotating ablation device may generate sufficient heat to weld the burr to the spring tip of the guide wire.

Given the considerations discussed above, it would be desirable to provide an ablation device that is easier to operate within selected parameters. The present invention fulfills this need, and provides further related advantages.

SUMMARY OF THE INVENTION

Briefly, the present invention provides an improved ablation assembly that is easier to operate within desirable operating parameters than conventional systems. In a preferred embodiment, the ablation assembly includes an advancer mechanism coupled to an ablation device, such as a rotatable burr. The advancer mechanism is moveable along a longitudinal path of motion to advance the ablation device from a first position adjacent a proximal end of a lesion to be ablated forward through the lesion.

In a preferred embodiment, the ablation assembly includes a rotatable burr coupled to a distal end of a driveshaft. A proximal end of the driveshaft is coupled to a drive assembly positioned within an advancer housing. The drive assembly is moveable from a first, retracted position, forward along a longitudinal path of motion. The coupling of the drive assembly to the driveshaft causes the burr to advance through a vessel lumen of a patient as the drive assembly is moved forward along its path of motion. A stop device is coupled to the housing, and is moveable from a first position to a second selected position along a path of motion that is parallel to the longitudinal path of motion of the drive assembly. The stop is securable to the housing at the second selected position. Furthermore, the stop has a flange that extends into the longitudinal path of motion of the drive assembly to a sufficient degree, such that as the drive assembly is moved forward, it contacts the flange, thereby stopping the forward motion of the drive assembly and associated burr.

Prior to performing an ablation procedure, the length of the lesion to be ablated is measured, for example, through the use of fluoroscopy, or any other procedure known in the art. A stop that extends into the longitudinal path of motion of the drive assembly or other advancer mechanism is secured at a location that is spaced forward from the starting position of the advancer mechanism by a length equal to the length of the lesion. As such, as the advancer mechanism is moved forward along the longitudinal path of motion, thereby advancing the burr through the lesion, the advancer mechanism moves a distance equal to the length of the lesion and hits the stop, which prevents further forward motion of the advancer mechanism. The burr coupled to the advancer mechanism moves a corresponding distance equal to the length of the lesion, which allows the cardiologist or other operator to cease operation of the device as soon as the burr clears the distal end of the lesion.

Alternatively, in a preferred embodiment, the stop is secured forward of the starting point of the advancer mechanism by a distance that is less than the length of the lesion by a small amount, such that when the advancer mechanism hits the stop, the operator knows that the burr is approaching the end of the lesion. It is then possible to release the stop, and slowly move the burr forward through the remainder of the lesion. By advancing through the end of the lesion at a slower rate than that used to proceed through the initial part of the lesion, the size of the rpm drop is reduced, and the unwanted effects associated with darting of the burr are minimized.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a side elevational view of an ablation assembly provided in accordance with a preferred embodiment of the present invention;

FIG. 2 is a front isometric view of a stop assembly used in the ablation assembly illustrated in FIG. 1;

FIG. 3 is a top plan view of a portion of the device shown in FIG. 1, illustrating a measurement device provided in accordance with the present invention;

FIG. 4 is a partial cross-sectional elevational view of the device illustrated in FIG. 1, showing the drive assembly in a first, retracted position; and FIG. 5 is a partial cross-sectional elevational view of the device illustrated in FIG. 1, showing the drive assembly in a second, forward position.

DETAILED DESCRIPTION OF THE PREFERRED EMBODIMENT

As illustrated in FIGS. 1 and 3–5, an ablation assembly 10 provided in accordance with a preferred embodiment of the present invention includes a drive assembly 11 positioned within a housing 12. The drive assembly 11 is moveable from a first retracted position 13 forward along a longitudinal path of motion 14 defined by shaft 20 extending through the length of the housing 12. (As used herein, the word "forward" shall refer to motion toward the left in the figures.) Although the drive assembly may be moved forward and back through a variety of devices, in a preferred embodiment, a knob 21 coupled to the drive assembly 11 extends upward through a first slot 23 provided in the housing 12. In use, a physician loosens the knob 21 in order to free the drive assembly in the housing. The drive assembly can then be advanced by moving the knob with respect to the housing to a desired position. The knob is then tightened to secure the drive assembly in the housing. Those skilled in the art will recognize that a number of releasably lockable mechanisms can be used in place of knob 21 such as, for example, clamps, latches, bolts, and snaps.

A proximal end 18 of a rotatable driveshaft 16 is coupled to the drive assembly. Although this may be achieved in a variety of ways, in a preferred embodiment, a "handshake" connector and catheter 33 are used, such as that found in the Rotablator™ system sold by Boston Scientific. A rotatable burr 15 is coupled to a distal end 17 of driveshaft 16. Activation of an air turbine in the drive assembly 11 transmits rotation to the driveshaft 16 and rotatable burr 15 to ablate unwanted material in a vessel lumen 19. In a preferred embodiment, a sheath 34 surrounds the driveshaft 16 and extends from the catheter 33 to a proximal end of the burr 15.

As further illustrated in FIGS. 2–5, a stop assembly 22 is coupled to housing 12. Stop assembly 22 is moveable along a path of motion that is parallel to the path of motion of drive assembly 11. In a preferred embodiment, stop assembly 22 is moveable from a first position substantially aligned with first retracted position 13 of drive assembly 11, to a second selected position 26. Stop assembly 22 has a flange 27 which extends into housing 12, into the longitudinal path of motion of drive assembly 11. A tightening cap 28 may be loosened to allow movement of stop assembly 22 along a second slot 24, and is tightened to secure stop assembly 22 in a selected position. In a preferred embodiment, as illustrated in FIG. 3, stop assembly 22 moves along a guide shelf 25 provided in housing 12, and a pair of bottom, end regions 37 of stop assembly 22 are rounded to provide a bearing surface against guide shelf 25. As will be discussed in greater detail below, as drive assembly or advancer mechanism 11 is moved forward along its path of motion, drive assembly 11 contacts flange 27 of stop assembly 22, which stops the forward motion of drive assembly 11.

As shown in FIG. 4, the cardiologist or other operator of ablation assembly 10 measures a length 31 of a lesion 30 positioned within vessel lumen 19 of a patient. This may be done via fluoroscopy or any other available method. Stop assembly 22 is secured to housing 12 via tightening cap 28 at a location spaced forward from first retracted position 13 of drive assembly 11 by a distance 32 equal to length 31 of lesion 30. In order to facilitate spacing of stop assembly 22 from the starting position of drive assembly 11, a series of marks 29 are provided on housing 12, as seen in FIGS. 1 and 3. The series of marks 29 may be spaced in accordance with any selected measurement system, for example, metric or British units. Also, an indicator 36 is coupled to stop assembly 22, to indicate the position of flange 27 within the interior of housing 12 against which drive assembly 11 will abut when moved forward.

In a typical procedure, rotatable burr 15 is advanced over a guide wire (not shown) to a location just proximal to lesion 30 as is known in the art, and as is illustrated in FIG. 4. The motor or turbine (not shown) is then activated, thereby beginning ablation of lesion 30. Drive assembly 11 is moved forward by grasping knob 21 and moving it forward, along with drive assembly 11 along longitudinal path of motion 14. When drive assembly 11 hits flange 27 of stop assembly 22, as illustrated in FIG. 5, forward motion of drive assembly 11 and the associated forward movement of burr 15 is stopped. Because distance 32 between the starting position of drive assembly 11 and stop assembly 22 is equal to the length of lesion 30, burr 15 will only be advanced by the length of lesion 30.

In an alternative preferred embodiment, distance 32 between the first or starting position of drive assembly 11 and stop assembly 22 is slightly less than length of lesion 30. As such, when the operator advances drive assembly 11 to stop assembly 22, the impact of drive assembly 11 against stop assembly 22 notifies the operator that burr 15 is approaching the end of lesion 30. The operator may then move stop assembly 22 further forward, and proceed to move the drive assembly at a relatively slow pace to advance burr 15 through the remainder of lesion 30. In so doing, an excessively large rpm drop is avoided, and darting of burr 15 is minimized. Although it would be possible to advance burr 15 slowly through the entire lesion 30, this process could be quite time-consuming, which is undesirable. By using an ablation assembly 10 provided in accordance with the present invention, an operator may move a burr quickly through substantially all of a lesion, but have warning as to when to limit forward motion of the burr.

From the foregoing, it will be appreciated that although embodiments of the invention have been described herein for purposes of illustration, various modifications may be made without deviating from the spirit of the invention. Thus, the present invention is not limited to the embodiments described herein, but rather is defined by the claims which follow.

The embodiments of the invention in which an exclusive property or privilege is claimed are defined as follows:

1. An ablation assembly comprising:
   a drive assembly positioned within a housing and moveable from a first, retracted position forward along a longitudinal path of motion the housing also including a guide shelf that extends parallel to the path of motion of the drive assembly;

a burr provided on a distal end of a driveshaft, a proximal end of the driveshaft being coupled to the drive assembly, such that movement of the drive assembly from the first retracted position forward causes the burr to advance through a vessel lumen of a patient; and a stop that is moveable within the housing from a first position to a second selected position along the guide shelf, the stop having a flange extending into the longitudinal path of motion of the drive assembly and a pair of bearing surfaces that ride within the guide shelf, the drive assembly contacting the flange as the drive assembly moves forward, thereby stopping forward motion of the drive assembly and burr.

2. The ablation assembly according to claim 1 further comprising a series of marks provided on the housing along the path of motion of the stop to indicate a measurement of a distance between the first position and the second selected position of the stop.

3. The ablation assembly of claim 1, wherein the stop further includes a tightening cap that can be selectively secured within a slot on the housing in order to secure the stop along the guide shelf.

4. The ablation assembly of claim 3, wherein the stop further includes an indicator that marks a distance that the drive assembly can be moved before contacting the flange on the stop.

* * * * *